United States Patent [19]

Engelhardt et al.

[11] Patent Number: 5,362,895
[45] Date of Patent: Nov. 8, 1994

[54] METHOD OF RECOVERING UNSATURATED FATTY ACIDS

[75] Inventors: Heinz Engelhardt, Bübingen; Rudolf Krumbholz, Merchweiler; Peter Lembke, Eschringen, all of Germany

[73] Assignee: K.D. Pharma GmbH, Bexbach, Germany

[21] Appl. No.: 25,041

[22] Filed: Mar. 1, 1993

[30] Foreign Application Priority Data

Mar. 2, 1992 [DE] Germany .................. 4206539

[51] Int. Cl.$^5$ ............................. C11B 3/10
[52] U.S. Cl. ............................. 554/175; 554/184; 554/185; 554/186; 554/191; 554/193; 554/205; 554/206
[58] Field of Search ............. 554/191, 193, 205, 185, 554/186, 184, 175

[56] References Cited

U.S. PATENT DOCUMENTS 5,013,433  5/1991  Higashidate et al. ............. 554/184

*Primary Examiner*—José G. Dees
*Assistant Examiner*—Dwayne C. Jones
*Attorney, Agent, or Firm*—Darby & Darby

[57] ABSTRACT

A method for recovering at least one unsaturated fatty acid having sixteen or more carbon atoms and/or at least one compound of such a fatty acid from a mixture derived from vegetable, animal or marine sources is provided. Fatty acids and/or fatty acid compounds of the mixture, in free acid or esterified form, are passed into a mobile phase of liquid carbon dioxide in a column over a stationary phase. The stationary phase contains a support and a material bound to the support which contains at least one free electron pair and/or multiple bond. After eluting any saturated fatty acid or fatty acid compound of the same number of carbon atoms from the column, the unsaturated fatty acid and/or fatty acid compound is recovered in pure chemical form or as an enriched mixture.

9 Claims, 11 Drawing Sheets

STANDARD FATTY ACID MIXTURE
STATIONARY PHASE: OCTADECYL, 50°C, 130 bar, 50%

STANDARD FATTY ACID MIXTURE
STATIONARY PHASE: AMINOPROPYL, 40°C, 135 bar, 50‰

STANDARD FATTY ACID MIXTURE
STATIONARY PHASE: TETRACHLOROPHTHALIMIDE, 40°C, 205 bar, 50%

BUTTER
STATIONARY PHASE: OCTADECYL, 50°C, 130 bar, 50%

BUTTER
STATIONARY PHASE: AMINOPROPYL, 40°C, 125 bar, 50%

BUTTER
STATIONARY PHASE: TETRACHLOROPHTHALIMIDE, 50°C, 128 bar, 50%

OIL FROM ALGAE
STATIONARY PHASE: AMINOPROPYL, 40°C, 135 bar, 50%

AVOCADO OIL
STATIONARY PHASE: AMINOPROPYL, 40°C, 150 bar, 50%

SALMON OIL
STATIONARY PHASE: AMINOPROPYL, 34°C, 110 bar, 46%

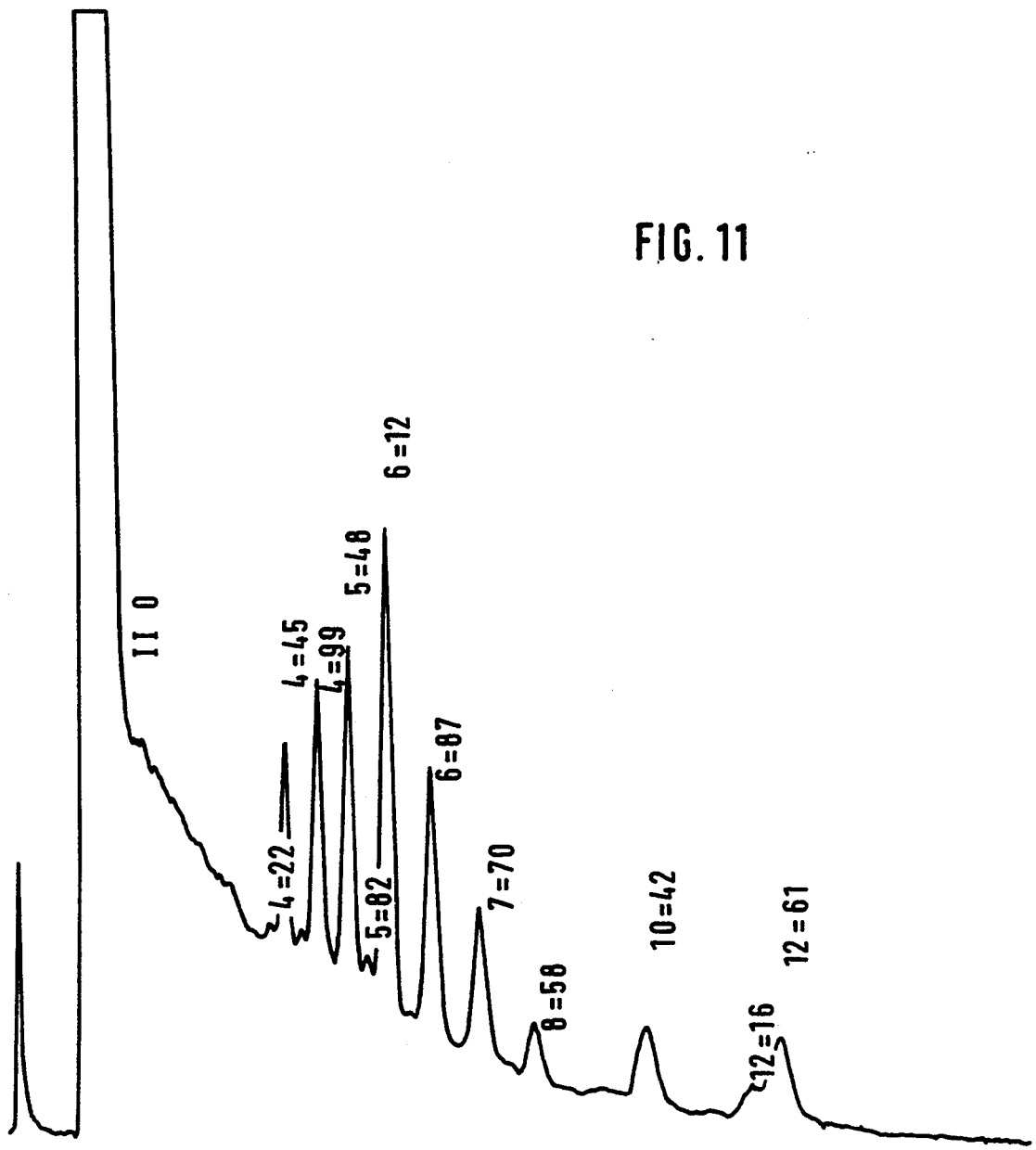

METHOD OF RECOVERING UNSATURATED FATTY ACIDS

The invention relates to a method of recovering at least one unsaturated fatty acid with sixteen or more carbon atoms in the molecule and/or at least one compound of such a fatty acid from a mixture composed of vegetable or animal fatty acids and/or fatty acid compounds.

BACKGROUND OF THE INVENTION

Unsaturated fatty acids are hydrocarbons in which one of the hydrogen atoms has been replaced by a carboxyl group (COOH) and which contain one or more double bonds between carbon atoms. These acids, particularly essential fatty acids such as linoleic, linolenic and arachidonic acids, play an important role in nutrition. Unsaturated fatty acids are derived commercially from vegetable, animal, and marine sources, particularly fish oils, by conventional solvent extraction methods. The solvents used for the extraction, such as benzene, dichloromethane or acetonitrile, are expensive and leave behind an undesirable and, in some cases, poisonous residue. Thus, a safe and inexpensive method which eliminates the aforementioned deficiencies is needed in the art.

SUMMARY OF THE INVENTION

The present invention provides a method for recovering unsaturated fatty acids and fatty acid compounds from a mixture, without contamination by foreign matter such as glycerides. As defined herein, fatty acid compounds refer to derivatized fatty acids which are generally found in fats. Examples of fatty acid compounds include mono-, di-, or fatty acid triglycerides.

According to the invention, a mixture of fatty acids and/or fatty acid compounds, in free acid or transesterified form, are passed in a mobile phase of supercritical or liquid carbon dioxide into a column containing a stationary phase. The stationary phase is composed of a support and a material bound to the support which contains at least one free electron pair and/or at least one multiple bond. After passage of the mixture through the column, undesired saturated fatty acids and their derivatives are eluted and unsaturated fatty acids and/or the unsaturated fatty acid compounds are recovered in pure form or in an enriched mixture form. Carbon dioxide solvent volatilizes from the eluate, leaving no toxic residue.

DESCRIPTION OF THE FIGURES

FIG. 11 illustrates the separation of unsaturated fatty acids from cod liver oil on an aminopropyl stationary phase.

DETAILED DESCRIPTION OF THE INVENTION

Figure 1:
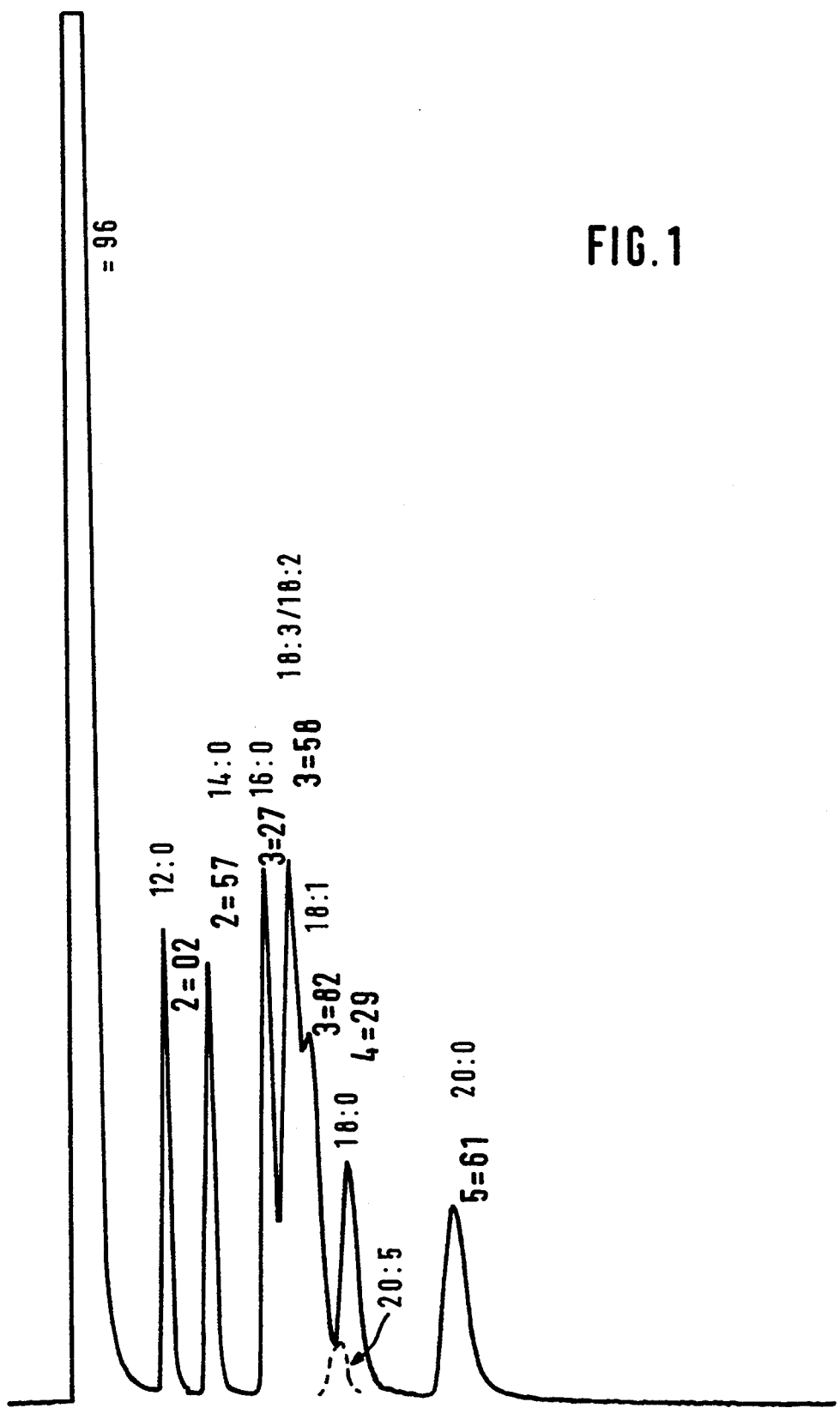
FIG. 1 illustrates the separation of a standard mixture of fatty acids on a stationary phase composed of silica gel having an octadecyl phase ($C_{18}H_{37}$).

The present invention provides a method for recovering unsaturated fatty acids or compounds thereof from mixtures derived from vegetable, animal, and/or marine sources in pure chemical form or enriched mixtures. It has been discovered, unexpectedly, that unsaturated fatty acids having sixteen or more carbon atoms (in free acid or esterified form) can be readily separated from mixtures using supercritical or liquid carbon dioxide as the mobile phase and a stationary phase having a support and a material bound to the support which has at least one free electron pair and/or multiple unsaturated bond.

The method of the invention permits separation of mixtures of unsaturated fatty acids such as oleic acid (18:1—in which the first number is the number of carbon atoms and the second number is the number of unsaturated bonds); eicosanoic acid (20:0); linoleic acid (18:2); linolenic acid (18:3); arachidonic acid (20:4); eicosapentaenoic acid (20:5); docosapentaenoic acid (22:5); and docosahexaenoic acid (22:6) in consecutive order. These fatty acids are typically found in sources such as cod liver, salmon, avocado, algae oils and butter.

In practicing the method of the invention, conventional separation equipment such as preparative and/or production scale high performance liquid chromatography apparatus are used. Such equipment is commerically available from a variety of sources including Prochrom S.A. (B.P. 9, F-54250 Champigneulles, France) and Prochrom Inc. (Indianapolis, Ind., USA).

Carbon dioxide ($CO_2$) is obtained as a by-product of many commercial processes and is used as a solid (dry ice), liquid, or gas. Carbon dioxide may be liquid at various temperatures by compressing it to liquification pressures and by removing the heat of condensation. In practicing the method of the invention, suitable temperature and pressure ranges are chosen which are sufficient to assure that carbon dioxide remains in its supercritical or liquid state under separation conditions.

In general, the method of the present invention is performed at temperatures ranging between about $-36.6°$ C. to about 100° C., preferably between about 25° C. and about 50° C., and most preferably around room temperature, e.g. 25° C. The pressures generally range between about 40 and about 250 bar, preferably between about 125 and about 205 bars. The flow rate may vary according to the degree of desired separation. Flow rate ranges of between about 40 and about 55%, particularly between about 45 and 55%, are useful in practicing the invention.

By optimizing pressure and temperature conditions, the method can be adapted further to the particular case. For example, temperature increases drive the eluates of the different fatty acids apart and can therefore lead to a desired separation in particular instances. Pressure increases push the eluates together and can be used to accelerate separation in cases where the desired eluate is sufficiently spaced apart from the proceeding and the following eluates.

The fatty acid mixtures may be dissolved directly or as a solution, e.g. a hexane solution, into the supercritical or liquid carbon dioxide mobile phase prior to its introduction into a column containing a stationary phase. The stationary phase is comprised of a solid support, e.g. silica gel or aluminum oxide, and a material bound to the support which provides at least one free electron pair and/or a multiple unsaturated bond. If desired, mixtures of different stationary phases may be used in practicing the invention. Representative examples of phases having free electron pairs include amino, alkylamino and nitro groups. Representative examples of phases having a multiple unsaturated bond include phenyl, cyano, alkyl cyano, and tetrachlorophthalimide. In practicing the invention, a stationary support having an aminopropyl phase is particularly preferred.

The stationary phases useful in practicing the method of the present invention are commercially available and may be purchased from a variety of companies including Macherey-Nagel (P.O. Box 307, D-5160 Dueren, Germany); Bischoff-Analysentechnick und -gerate GmbH (Boeblinger Strasse 23, D-7250 Leonburg, Germany); Merck (Frankfurter Strasse 250, D-6100 Darmstadt 1, Germany); and Alltech GmbH (Suedstrasse 8, D-8023 Unterhaching, Germany). Preparation of tetrachloride phthalimide stationary phases has been described in the literature, e.g., Klaus Jost, Masters Thesis, Saarbruecken, 1981; and Alfons Roth, Disserration, Saarbruecken, 1987. These references are incorporated by reference in their entirety.

Without being bound by any theory of operation for the invention, it is believed that separation of unsaturated fatty acids or their derivatives is due to an electronic interaction between the free electron pair or the $\pi$ electrons of the multiple bond in the stationary phase with the $\pi$ electrons of the double bonds in the unsaturated fatty acids. As a result of this $\pi$—$\pi$ interaction, the unsaturated fatty acids are held longer on the stationary phase during passage through the column than are the saturated fatty acids. The longer unsaturated fatty acid retention time allows for removal of saturated fatty acids and promotes separation between the unsaturated fatty acids.

Saturated fatty acids are retained more strongly, relative to unsaturated fatty acids, on stationary phases having bound long alkyl chains, e.g. octadecyl, which are usually employed in analytical separations. This effect may be due to stronger van der Waal's interactions occurring between the saturated alkyl chains of the stationary phase and the fatty acid. The octadecyl stationary phase, however, does not permit separation of unsaturated fatty acids, e.g. monounsaturated and polyunsaturated fatty acids having between eighteen and twenty carbon atoms, because of overlapping between eluates during chromatographical procedures. Stationary phases having short alkyl chains of two to eight carbon atoms, however, are useful in separating unsaturated fatty acids and such phases may be used in practicing the invention. These stationary phases are also commercially available from the above listed sources.

If desired, fatty acid mixtures containing fatty acid triglycerides can be subjected to the method of the present invention to separate the fatty acids from the triglycerides. The triglycerides can then be hydrolyzed under acidic or alkaline conditions and the resulting mixture can be subjected to the method of the present invention to recover additional fatty acids.

Unsaturated fatty acids recovered by the method of the present invention are useful in a variety of ways which include preparation of dietetic or pharmaceutical products. For example, recovered linoleic acid and linolenic acid (essential fatty acids which the human body cannot synthesize itself), and arachidonic acid, eicosapentaenoic acid and docosahexaenoic acid (omega-3-fatty acids which are believed to be capable of dissolving fat deposits in blood vessels) can be used as nutritional supplements.

The following Example illustrates the method of the present invention without limiting its scope.

EXPERIMENT

(a) Procedure

Unsaturated fatty acids were recovered from a standard synthetic mixture and from different natural fatty acid mixtures. Prior to separation, the fatty acids and/or fatty acid compounds were converted to the ethyl esters by conventional methods, e.g. acid catalyzed esterification or transesterification with ethanol. The esterified fatty acid mixture was dissolved in hexane and the solution was introduced into liquid carbon dioxide. The carbon dioxide mixture was then introduced separately into columns containing silica gel having different stationary phases in different experiments. The column consists of a stainless steel tube (25 cm length, 4 cm internal diameter) which was held below the supercritical carbon dioxide by appropriate arrangements. The pressure of the carbon dioxide and the temperature were varied in different experiments. Samples of fatty acid mixtures were introduced into the column by means of a conventional rheodyne valve.

Chromatograms of the collected eluates are reproduced in FIGS. 1 to 11 along with an identification of the fatty acid mixture and conditions (the stationary phase, the temperature in °C., the pressure in bar and the flow rate in %). The retention time (minutes) and/or identity of the fatty acid constituent are indicated on the individual peaks.

(b) Separation of a Standard Fatty Acid Mixture on a Octadecyl Stationary Phase A standard mixture of fatty acids was introduced onto a stationary phase having a silica gel support and a bound octadecyl phase ($C_{18}H_{37}$). The constituents of the mixture are as follows:

40 $\mu$g of ethyl laurate (12:0)
41 $\mu$g of ethyl myristate (14:0)
45 $\mu$g of ethyl palmirate (16:0)
51 $\mu$g of ethyl linoleate (18:2)
55 $\mu$g of ethyl linolenate (18:3)
48 $\mu$g of ethyl oleate (18:1)
60 $\mu$g of ethyl stearate (18:0)
46 $\mu$g of ethyl eicosanate (20:0)

FIG. 1 is a chromatogram showing separation of the standard mixtures from the octadecyl column. The first and largest peak, drawn here after 0.96 minutes, is the hexane solvent. This is also true of all other experiments.

The saturated fatty acids (12:0), (14:0) and (16:0) follow. After (16:0) and before (18:0), (18:3) and (18:8) eluate almost simultaneously and, overlapping these closely, (18:1) comes next and (20:0) follows as the last saturated fatty acid. The unsaturated fatty acids (20:4), (20:5) and even (22:6) appeared before (20:0). It is interesting to note that eicosapentaenoic acid (20:5), shown by a broken line, eluates in a mixture composed mainly of stearic acid and oleic acid.

Figure 2:
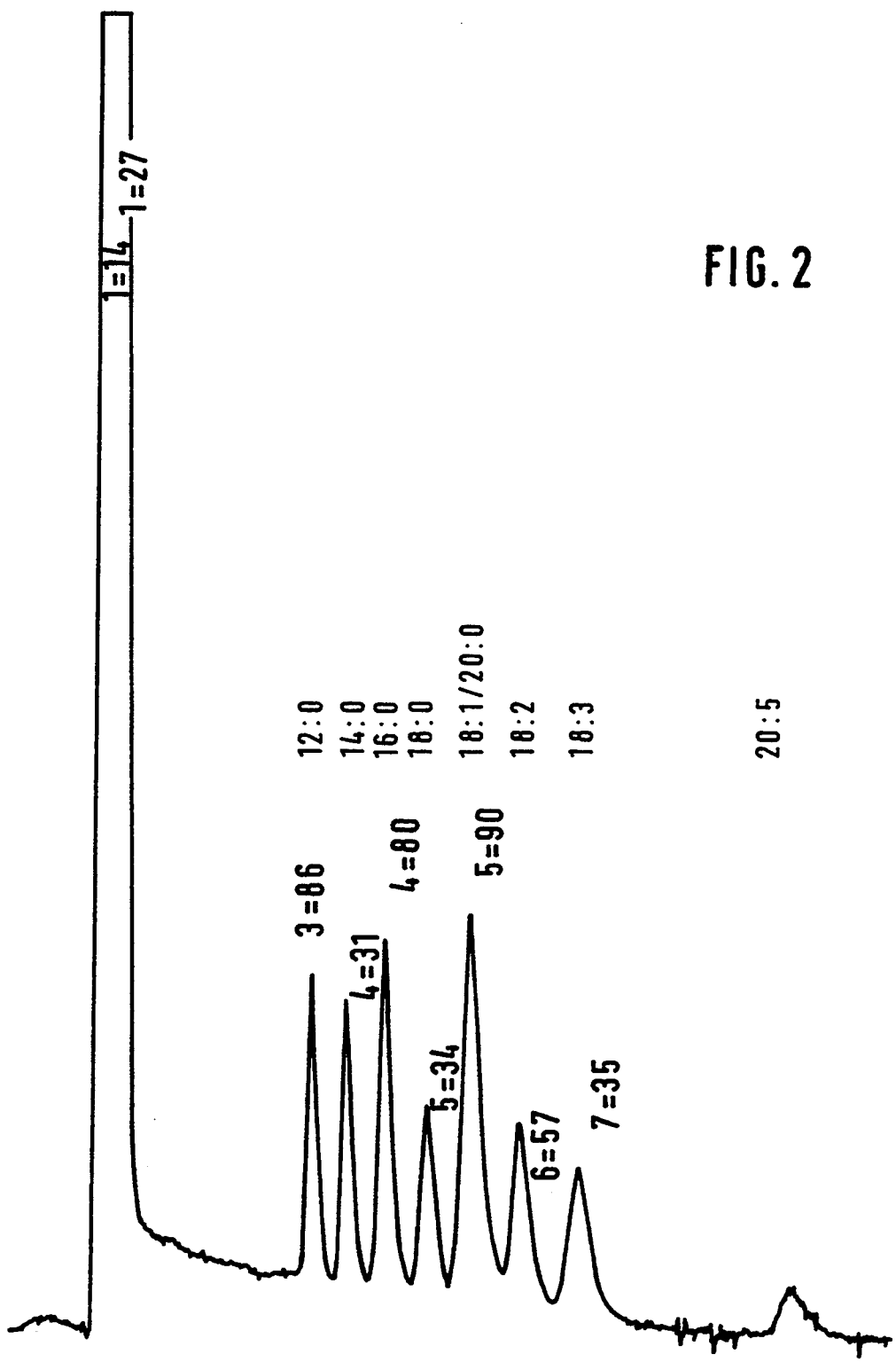
FIG. 2 illustrates the separation of a standard mixture of fatty acids on a stationary phase composed of an aminopropyl phase. Eicosapentaenoic acid has been added to the standard mixture.

(c) Separation of a Standard Fatty Acid Mixture on a Aminopropyl Stationary Phase A standard mixture of fatty acids of part (b) with added eicosapentaenoic acid was introduced onto a stationary phase having a silica gel support and a bound aminopropyl phase. A chromatograph of the separation is shown in FIG. 2. In this case, fatty acid (18:0) directly follows (16:0) and (18:1); fatty acids (18:2) and (18:3) eluate in this sequence after (18:0); and fatty acid (18:1) eluating as a mixture with (20:0). The linoleic acid, linolenic acid and eicosapentaenoic acid are separated from one another essentially up to the base line.

(d) Separation of a Standard Fatty Acid Mixture on a Tetrachlorophthalimide Stationary Phase The standard mixture of fatty acids of part (b) was introduced onto a stationary phase having a silica gel support and a bound tetrachlorophthalimide phase. A chromatograph of the separation is shown in FIG. 3.

As shown in this Figure, fatty acids (18:1), (18:2) and (18:3) elute after fatty acid (18:0) and (18:3) and are fairly well separated. The eluates can be further separated at a lower pressure and a higher temperature.

Figure 3:
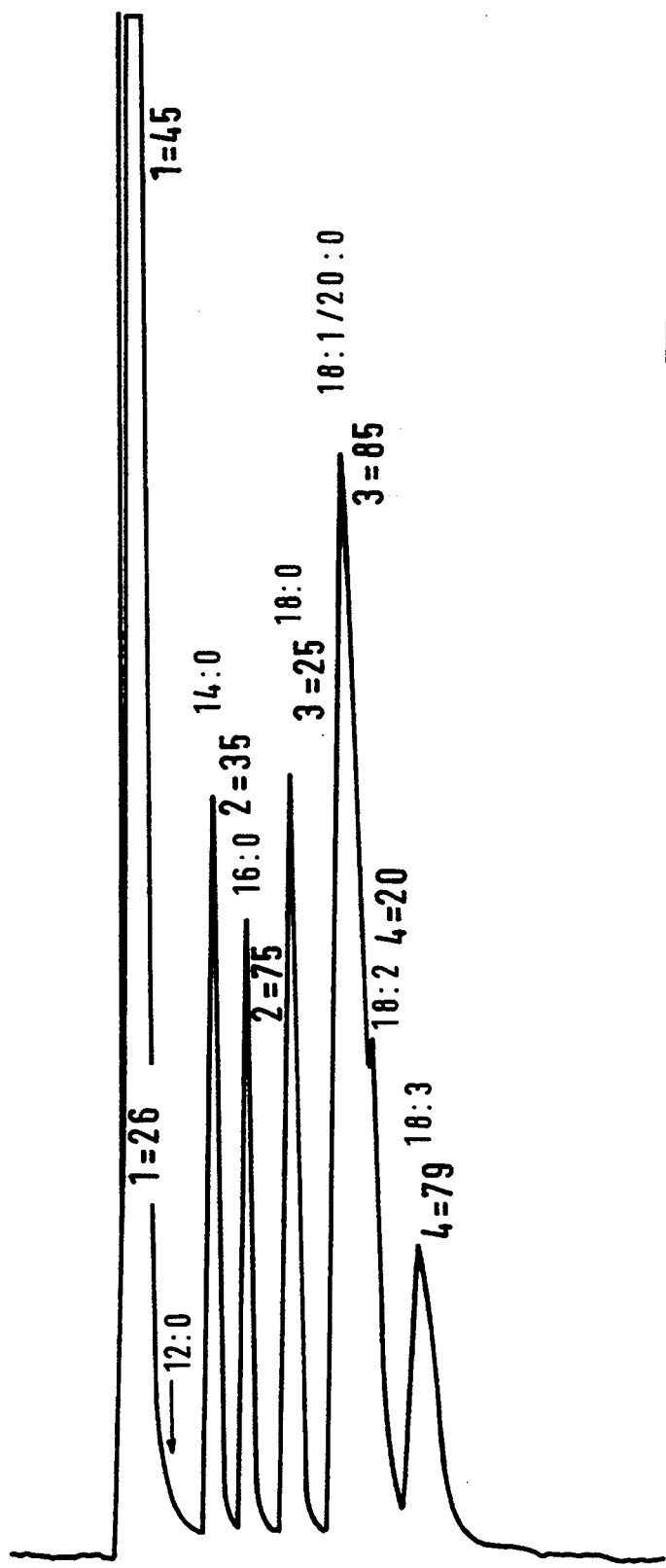
FIG. 3 illustrates the separation of a standard mixture of fatty acids on a stationary phase composed of a tetrachlorophthalimide phase.
Figure 4:
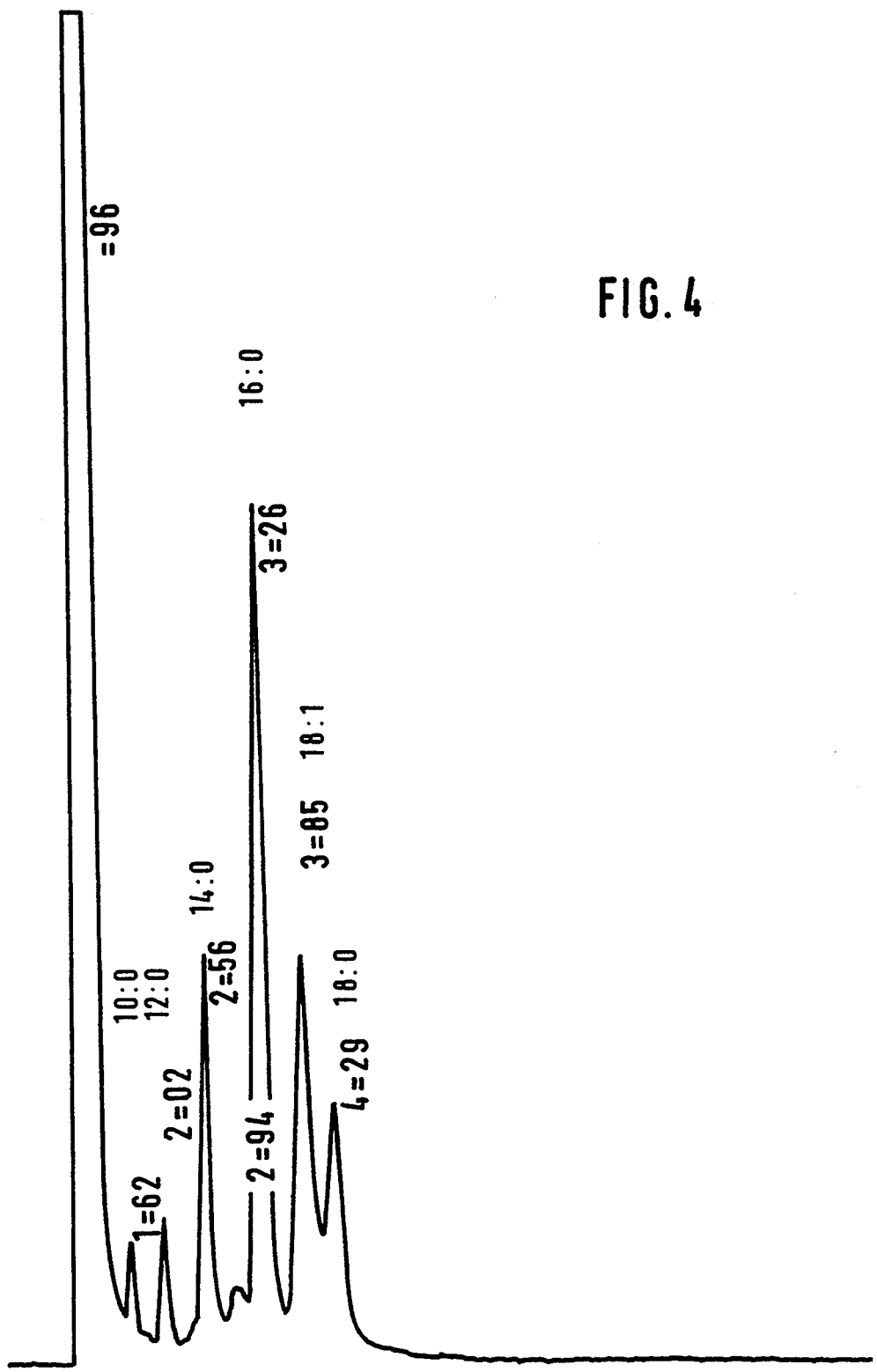
FIGS. 4 to 6 correspond to FIGS. 1 to 3, respectively, however, they illustrate the separation of fatty acids from butter on an octadecyl (FIG. 4); an aminopropyl (FIG. 5); and a tetrachlorophthalimide (FIG. 6) stationary phase.
Figure 5:
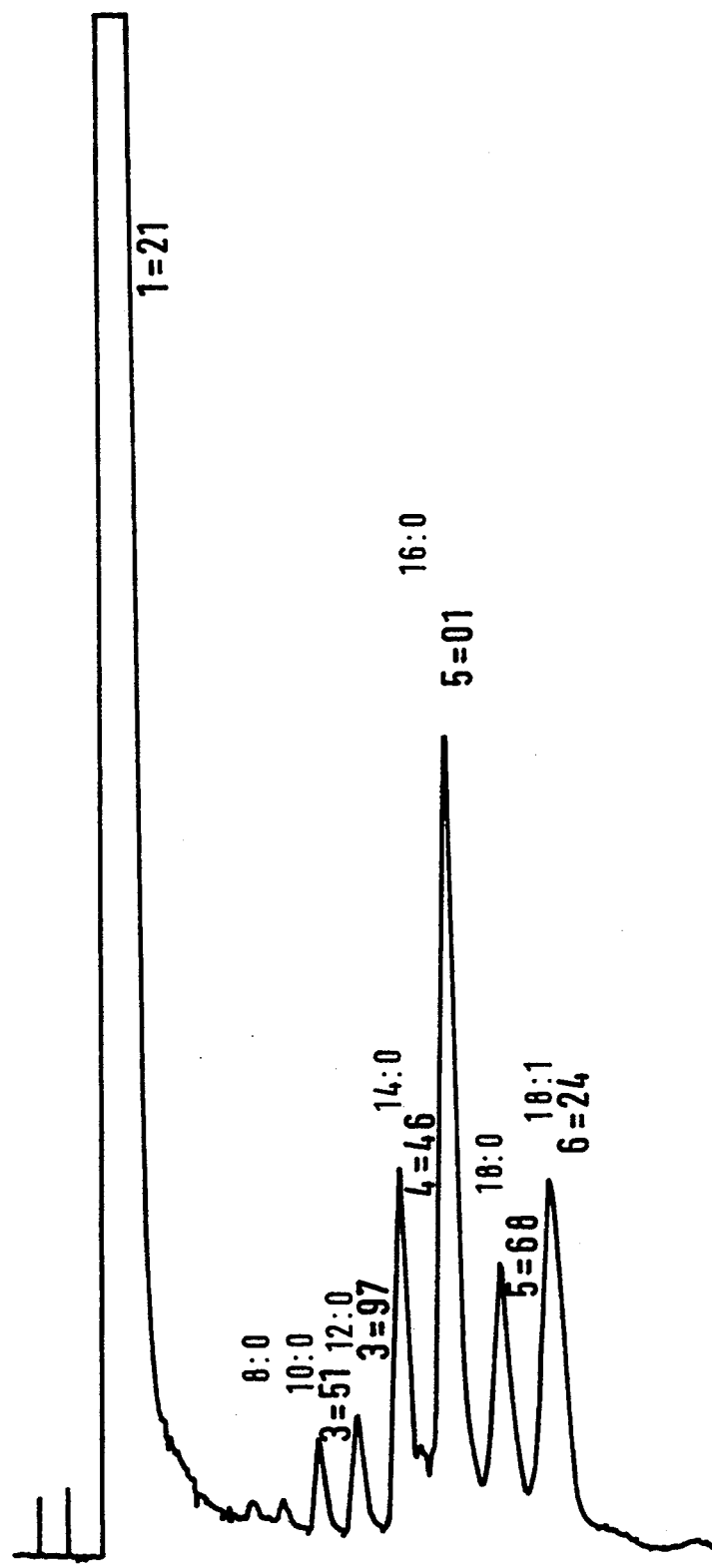
Figure 6:
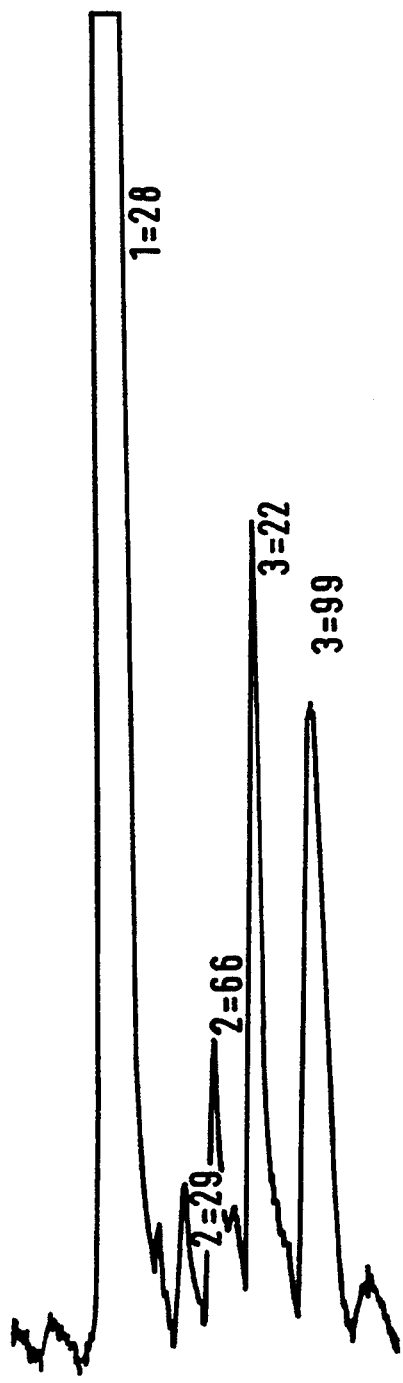

(e) Separation of Unsaturated Fatty Acids from Butter on Various Stationary Phases FIGS. 4 to 6 correspond to FIGS. 1 to 3; however, they show the relationships for a natural mixture of fatty acids, namely from butter. These experiments are merely of theoretical interest. The oleic acid can still be separated, as shown by FIG. 5.

Figure 7:
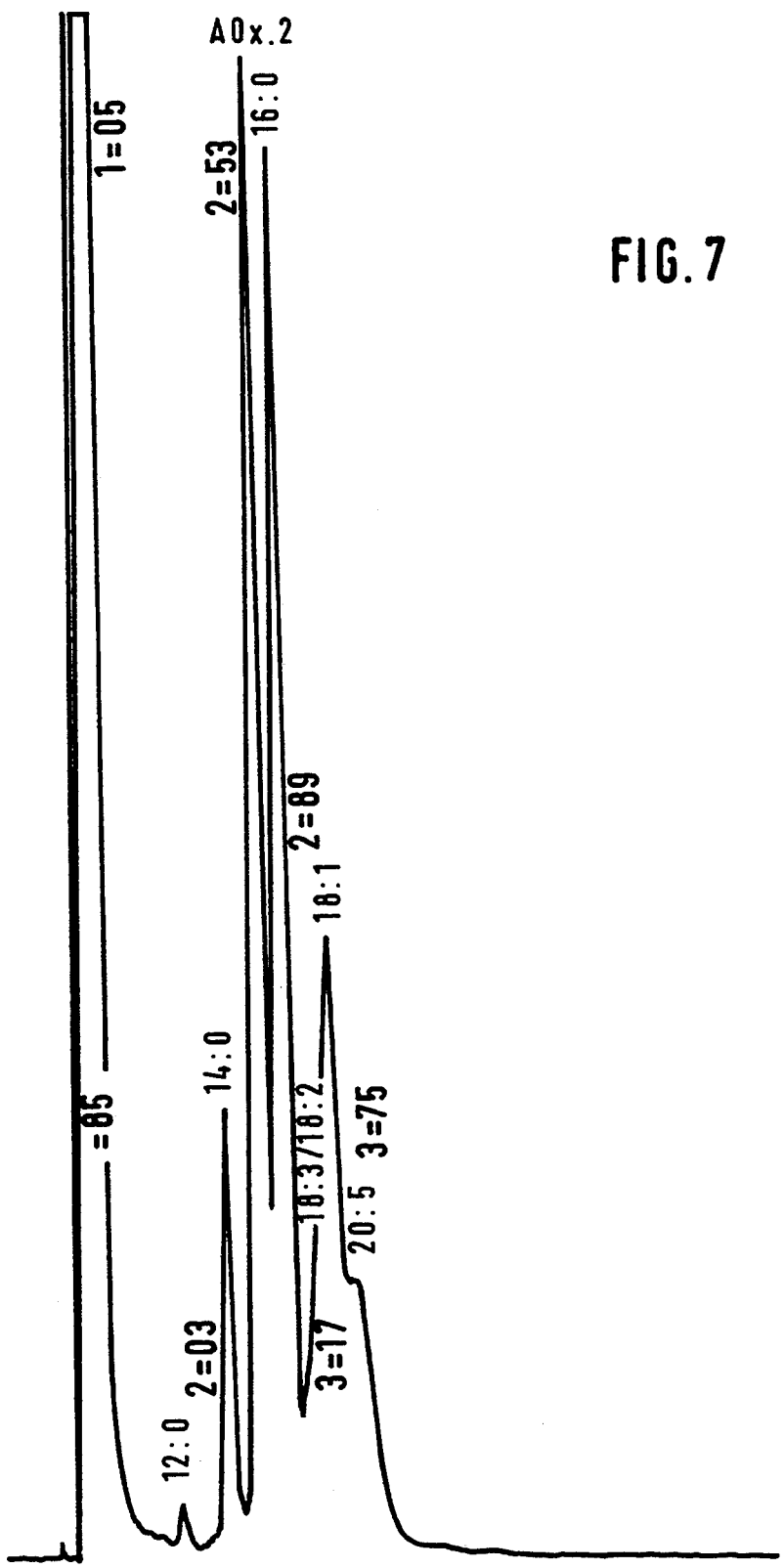
FIGS. 7 and 8 illustrate the separation of unsaturated fatty acids in algae oil on an octadecyl (FIG. 7) and an aminopropyl (FIG. 8) stationary phase.
Figure 8:
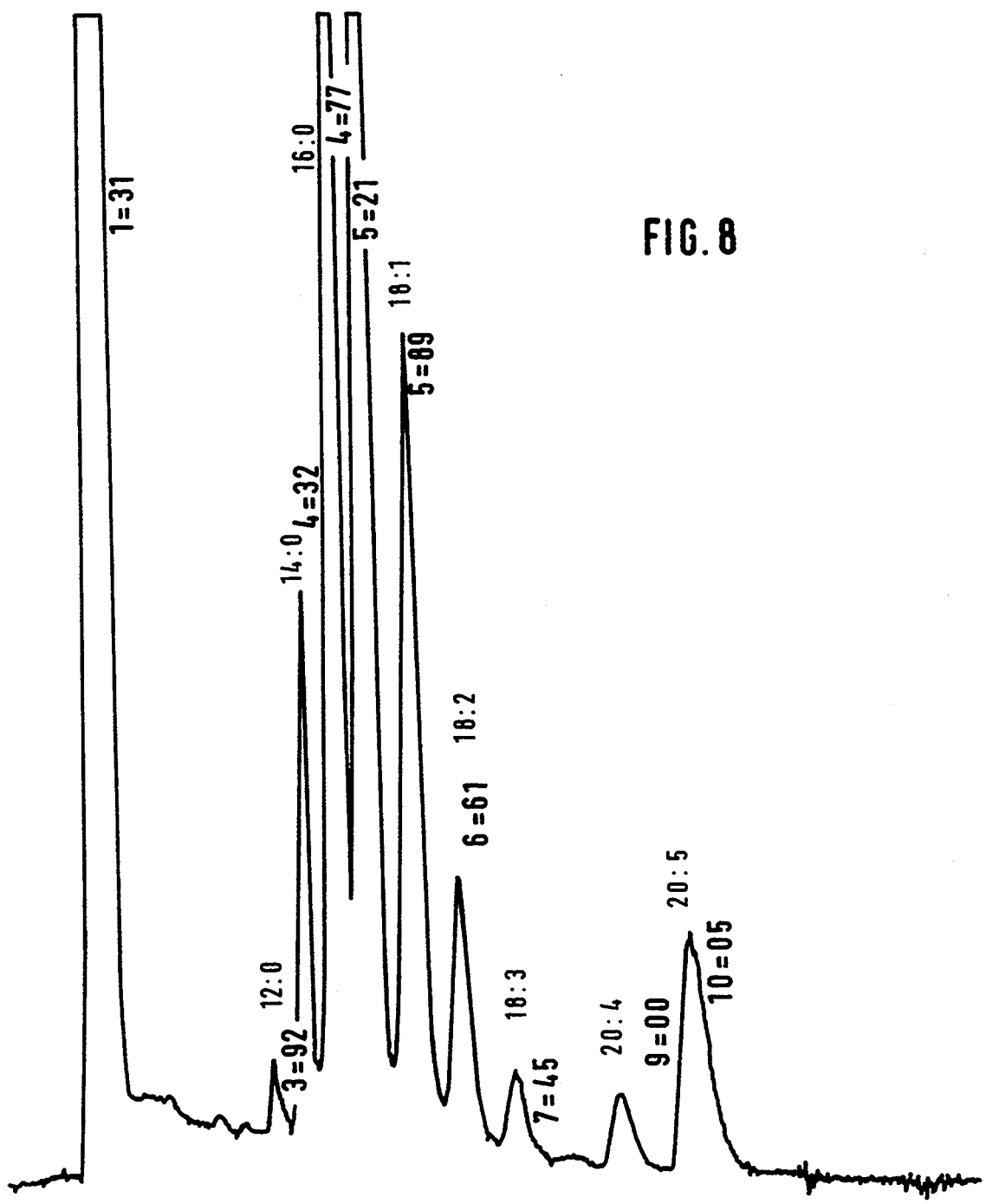

(f) Separation of Unsaturated Fatty Acids from Algae Oil on a Octadecyl Stationary Phase Algae oil served as a starting material for the recovery of eicosapentaenoic acid as well as of arachidonic acid and, if the method is optimized, possibly also for the recovery of linoleic and linolenic acids. The eicosapentaenoic acid peak, which is only partially resolved as indicated in FIG. 7, is completely isolated in FIG. 8. The same is true for the arachidonic acid peak (compare FIG. 7).

Figure 9:
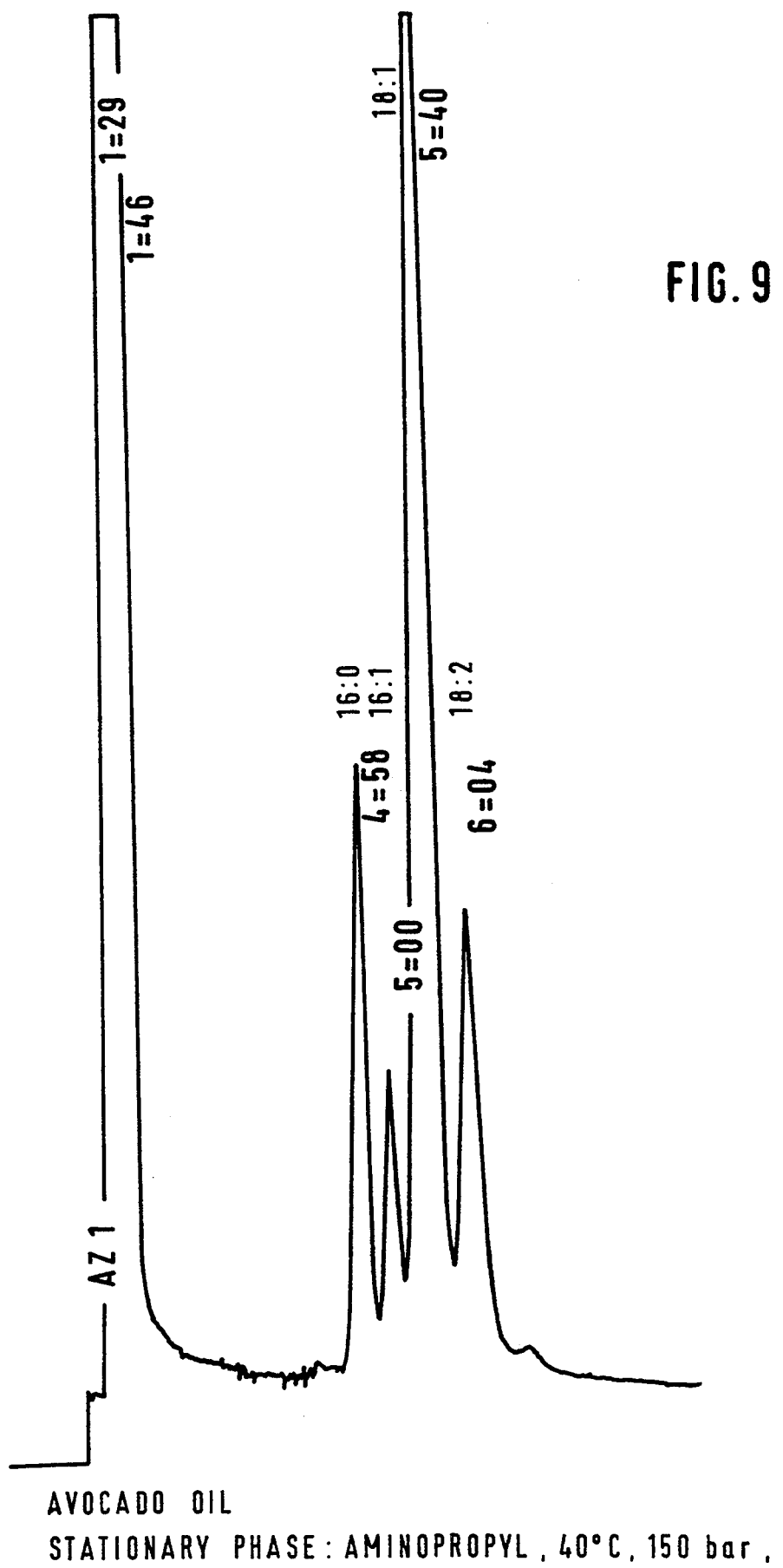
FIG. 9 illustrates the separation of unsaturated fatty acids in avocado oil on an aminopropyl stationary phase.

(g) Separation of Unsaturated Fatty Acids from Avocado Oil on an Aminopropyl Stationary Phase FIG. 9 shows that oleic acid and linoleic can be recovered from avocado oil. The treatment conditions can be optimized by raising the temperature and lowering the pressure so as to pull apart the eluates.

Figure 10:
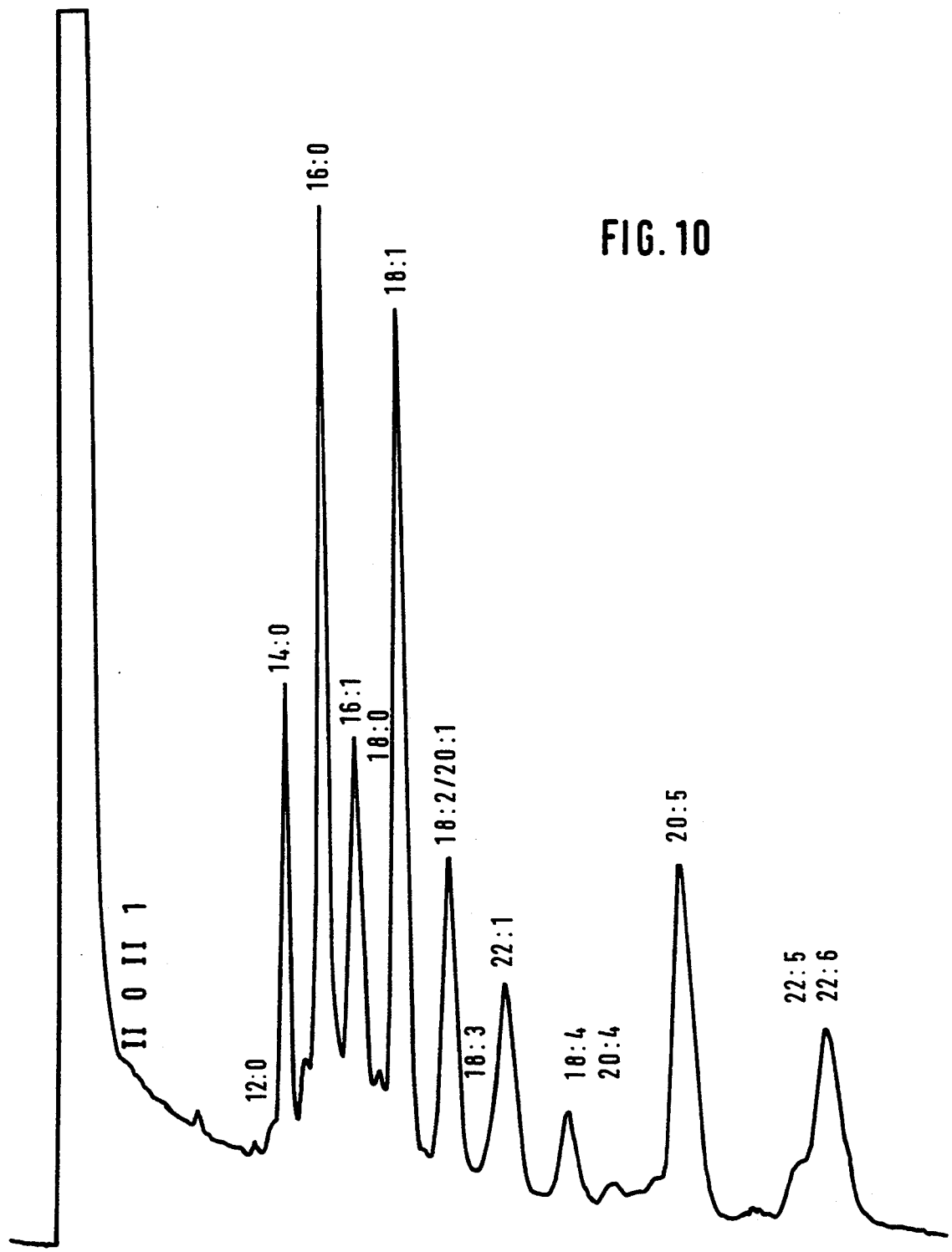
FIG. 10 illustrates the separation of unsaturated fatty acids from salmon oil on an aminopropyl stationary phase.

(h) Separation of Unsaturated Fatty Acids from Salmon Oil on an Aminopropyl Stationary Phase FIG. 10 shows the suitability of salmon oil as a starting material for the recovery of eicosapentaenoic acid, docosaenoic acid (22:1), a mixture of docosahexaenoic acid (22:6) with docosapentaenoic acid (22:5), a mixture of linolenic acid (18:2) and eicosaenoic acid (20:1) as well as, to a lesser extent, further unsaturated fatty acids.

(h) Separation of Unsaturated Fatty Acids from Salmon Oil on an Aminopropyl Stationary Phase Unsaturated fatty acids can also be obtained from cod liver oil using the method of the present invention as shown by the chromatogram of FIG. 11.

We claim:

1. A method of recovering an unsaturated fatty acid comprising sixteen or more carbon atoms or a derivative thereof from a mixture comprising:
   (a) passing a mixture comprising an unsaturated fatty acid, a saturated fatty acid, mixtures thereof, or derivatives thereof in a mobile phase of supercritical or liquid carbon dioxide into a column containing a stationary phase comprising a support and an organic material bound to the support having at least one free electron pair, a multiple bond, or a combination thereof;
   (b) eluting the saturated fatty acid and/or derivative thereof from said column; and
   (c) recovering said unsaturated fatty acid from said column.

2. The method according to claim 1, wherein said unsaturated and saturated fatty acids and derivatives thereof are converted into ethyl esters prior to step (a).

3. The method according to claim 1, wherein said mixture is in solution prior to passage into the mobile phase.

4. The method according to claim 1, wherein the material bound to the support contains an amino group or a nitro group.

5. The method according to claim 1, wherein the material bound to the support contains a phenyl group, a cyano group or a mixture thereof.

6. The method according to claim 1, wherein the material bound to the support contains an alkyl group having two to eight carbon atoms.

7. The method according to claim 1, wherein the material bound to the support contains an aminopropyl, tetrachlorophthalimide, or a mixture thereof.

8. The method according to claim 1, wherein the material bound to the support contains a cyanopropyl group.

9. A method of recovering an unsaturated fatty acid comprising sixteen or more carbon atoms or a derivative thereof from a mixture, consisting essentially of the following steps:
   (a) passing a mixture comprising an unsaturated fatty acid, a saturated fatty acid, mixtures thereof, or derivatives thereof in a mobile phase of supercritical or liquid carbon dioxide into a column containing a stationary phase comprising a support and a material bound to the support, wherein the material bound to the support is one or a combination of: materials with at least one free electron pair, selected from the group consisting of amino, alkylamino and nitro groups, and materials with a multiple unsaturated bond, selected from the group consisting of phenyl, cyano, and tetrachlorophthalimide groups;
   (b) eluting the saturated fatty acid and/or derivative thereof from said column; and
   (c) recovering said unsaturated fatty acid from said column.

* * * * *